United States Patent
Smith et al.

(10) Patent No.: US 11,707,616 B2
(45) Date of Patent: Jul. 25, 2023

(54) FLOW STOP DEVICE

(71) Applicant: CareFusion 303, Inc., San Diego, CA (US)

(72) Inventors: Jake Smith, Yorba Linda, CA (US); Soon Park, Cypress, CA (US)

(73) Assignee: CAREFUSION 303, INC., San Diego, CA (US)

( * ) Notice: Subject to any disclaimer, the term of this patent is extended or adjusted under 35 U.S.C. 154(b) by 959 days.

(21) Appl. No.: 16/597,734

(22) Filed: Oct. 9, 2019

(65) Prior Publication Data

US 2021/0106806 A1   Apr. 15, 2021

(51) Int. Cl.
*A61M 39/28* (2006.01)

(52) U.S. Cl.
CPC .................. *A61M 39/285* (2013.01)

(58) Field of Classification Search
CPC ... A61M 39/285; A61M 39/284; A61M 39/28
See application file for complete search history.

(56) References Cited

U.S. PATENT DOCUMENTS

| | | |
|---|---|---|
| 2,832,560 A | 4/1958 | Grigsby |
| 5,865,813 A | 2/1999 | DeKalb et al. |
| 2010/0056867 A1 * | 3/2010 | Labombard ........ A61B 1/00068 600/135 |
| 2018/0272062 A1 | 9/2018 | Yu |

OTHER PUBLICATIONS

Oxford Dictionary definition for "protrusion", available at https://www.oxfordlearnersdictionaries.com/us/definition/english/protrusion and accessed Nov. 17, 2022 (Year: 2022).*
International Search Report and Written Opinion for Application No. PCT/US2020/054105, dated Jan. 28, 2021, 13 pages.

* cited by examiner

*Primary Examiner* — Amber R Stiles
*Assistant Examiner* — Nelson Louis Alvarado, Jr.
(74) *Attorney, Agent, or Firm* — Morgan, Lewis & Bockius LLP (57) ABSTRACT

Flow stop assemblies are described herein. A flow stop assembly configured to control flow through a tubing includes a flow stop base and a pincher. The flow stop base includes a base wall, at least one pincher guard, a tubing guide, a pincher recess, a pincher protrusion, and a base extension. The pincher is movable relative to the base extension and is configured to move between a flow position and an occlusion position, wherein in the flow position the pincher surface is spaced apart from the pincher protrusion and in the occlusion position, the pincher surface is disposed adjacent to the pincher protrusion and is configured to obstruct flow through the tubing.

17 Claims, 6 Drawing Sheets

FLOW STOP DEVICE

FIELD OF THE INVENTION

The present disclosure generally relates to flow control devices, and, in particular, to flow control devices for tubing.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. During use, the flow of medical fluid through tubing may be occluded with pinch clamps to control the flow of the medical fluid. Often, pinch clamps are designed for a specific tube size.

In some applications, variations in tube size may hinder the performance of the pinch clamp.

SUMMARY

The disclosed subject matter relates to flow stop assemblies. In certain embodiments, a flow stop assembly is disclosed that is configured to control flow through a tubing and comprises a flow stop base, and a pincher. The flow stop base includes a base wall extending from the flow stop base; at least one pincher guard extending from the base wall, wherein the at least one pincher guard is configured to be disposed around the tubing; a tubing guide configured to receive the tubing, wherein the at least one pincher guard and the tubing guide are axially spaced apart and are configured to axially align the tubing through the flow stop base; a pincher recess defined between the base wall, the at least one pincher guard, and the tubing guide; a pincher protrusion disposed within the pincher recess and configured to be adjacent to the tubing, wherein the pincher protrusion extends from the base wall; and a base extension extending away from the pincher recess. The pincher is movable relative to the base extension and comprises a pincher surface, the pincher configured to move between a flow position and an occlusion position, wherein in the flow position the pincher surface is spaced apart from the pincher protrusion and in the occlusion position, the pincher surface is disposed adjacent to the pincher protrusion and is configured to obstruct flow through the tubing.

In certain embodiments, a flow stop assembly is disclosed that comprises a tubing defining a flow path, a flow stop base, and a pincher. The flow stop base includes a base wall extending from the flow stop base; at least one pincher guard extending from the base wall, wherein the at least one pincher guard is configured to be disposed around the tubing; a tubing guide configured to receive the tubing, wherein the at least one pincher guard and the tubing guide are axially spaced apart and are configured to axially align the tubing through the flow stop base; a pincher recess defined between the base wall, the at least one pincher guard, and the tubing guide; a pincher protrusion disposed within the pincher recess and configured to be adjacent to the tubing, wherein the pincher protrusion extends from the base wall; and a base extension extending away from the pincher recess. The pincher is movable relative to the base extension and comprises a pincher surface, the pincher configured to move between a flow position and an occlusion position, wherein in the flow position the pincher surface is spaced apart from the pincher protrusion and in the occlusion position, the pincher surface is disposed adjacent to the pincher protrusion and is configured to obstruct flow through the tubing.

In certain embodiments, a method is disclosed that comprises providing fluid flow through a tubing; actuating a pincher against the tubing to fold the tubing over a pincher protrusion; and obstructing the fluid flow through the tubing.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed flow stop assembly incorporates a pinching mechanism to fold tubing and occlude fluid flow therethrough. The pincher can be movable to fold the tubing over a pincher protrusion. By folding the tubing, flow within the tubing can be reliably occluded when using a wide variety of tubing sizes.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components may be shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the occlusion of medical fluid during the administration of medical fluid using the disclosed flow stop assembly, it is to be understood that this description is only an example of usage and does not limit the scope of the claims. Various aspects of the disclosed flow stop assembly may be used in any application where it is desirable to control the flow of fluid.

The disclosed flow stop assembly overcomes several challenges discovered with respect to certain conventional clamps. One challenge with certain conventional clamps is that certain conventional clamps are designed to be used with specific tubing sizes. Because variations in tubing sizes may hinder the performance of conventional clamps or require various sizes of conventional clamps, the use of conventional clamps is undesirable.

Therefore, in accordance with the present disclosure, it is advantageous to provide a flow stop assembly as described herein that allows for flow occlusion with a wide variety of tubing sizes. The disclosed flow stop assembly provides a folding mechanism that allows for reliable flow occlusion for a wide variety of tubing sizes.

An example of a flow stop assembly that allows for reliable flow occlusion is now described.

Figure 1:
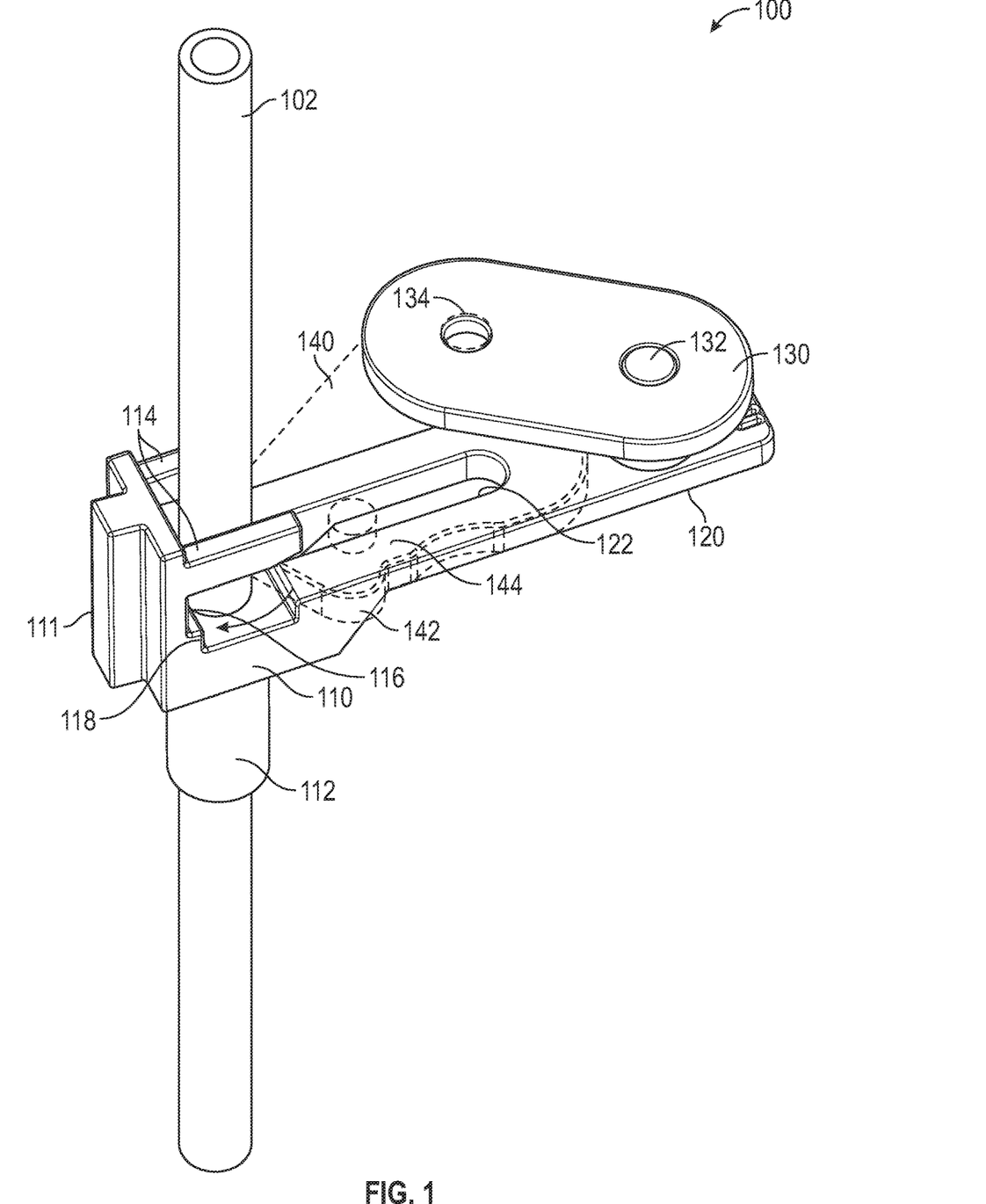
FIG. 1 is a perspective view of a flow stop assembly in a flow position, in accordance with various aspects of the present disclosure.

FIG. 1 is a perspective view of a flow stop assembly 100 in a flow position, in accordance with various aspects of the present disclosure. In the depicted example, the flow stop assembly 100 controls the flow of fluids such as medical fluids as they are delivered from a fluid source to a patient. As illustrated, medical fluid can be directed through a flow path defined by tubing 102. As can be appreciated, the tubing 102 can be of any suitable diameter needed for treatment.

During operation, the occlusion mechanism of the flow stop assembly 100 can be actuated to allow for fluid flow to be permitted or occluded by folding the tubing 102 to occlude flow therethrough. As illustrated, a portion of the tubing 102 passes through the flow stop base 110 to allow the flow stop assembly 100 to control flow through the tubing 102.

In some embodiments, tubing 102 extends through, and is axially aligned and/or retained by a pincher guard 114 and a tubing guide 112. In the illustrated embodiment, pincher guards 114 extend from a base wall 111 on either side of the tubing 102. The base wall 111 can extend vertically from the flow stop base 110 and include a rib to facilitate coupling with other components. The pincher guards 114 can prevent lateral movement of the tubing 102 during operation, including during pinching or occlusion operations.

A lower portion of the tubing 102 can pass through a tubing guide 112 formed in the flow stop base 110. The tubing guide 112 can be a cylindrical member configured to receive the tubing 102. The tubing guide 112 can be sized to prevent radial movement of the tubing 102 while allowing axial movement of the tubing 102. The tubing guide 112 and the pincher guard 114 can cooperatively axially align the tubing 102. In certain embodiments, the tubing 102 can be axially affixed or coupled within the tubing guide 112. As can be appreciated, the tubing guide 112 can be spaced apart from the pincher guards 114 to define a pincher recess 116 wherein the tubing 102 extends across the pincher recess 116. Further, the base wall 111 can define the pincher recess 116 and also prevent or restrict radial movement of the tubing 102.

In a flow position, the flow path defined within the tubing 102 is unobstructed to allow the flow of medical fluid. In some embodiments, the pincher surface 142 of the pincher 140 is spaced apart from the portion of the tubing 102 disposed within the pincher recess 116. As illustrated, the pincher 140 is rotated away from the tubing 102 disposed within the pincher recess 116. As described herein, the pincher 140 can rotate on a guide pin 144 disposed within a guide slot 122 formed within the base extension 120 of the flow stop base 110. As illustrated, the base extension 120 extends away from the pincher recess 116 of the flow stop base 110. The pincher 140, in some instances, can further translate along the guide slot 122. In some embodiments, the geometry of the guide slot 122 can determine the range of permitted travel of the pincher 140.

In the depicted example, the pincher 140 can be actuated or rotated by a mechanical or planar linkage, such as a three bar linkage or a four bar linkage. As illustrated, the pincher 140 can be actuated by rotating or moving the rocker 130. The rocker 130 can be rotatably coupled to the base extension 120 of the flow stop base 110. As illustrated, the rocker 130 can rotate about a rocker pivot 132 rotatably coupling the rocker 130 to the base extension 120. As the rocker 130 is rotated, the rocker 130 can actuate the pincher 140 to rotate and/or translate the pincher 140. In some embodiments, the rocker 130 can be rotatably coupled to the pincher 140 at a pincher link 134. During operation, the rocker 130 can be actuated by a clinician to actuate or rotate the pincher 140.

Figure 2:
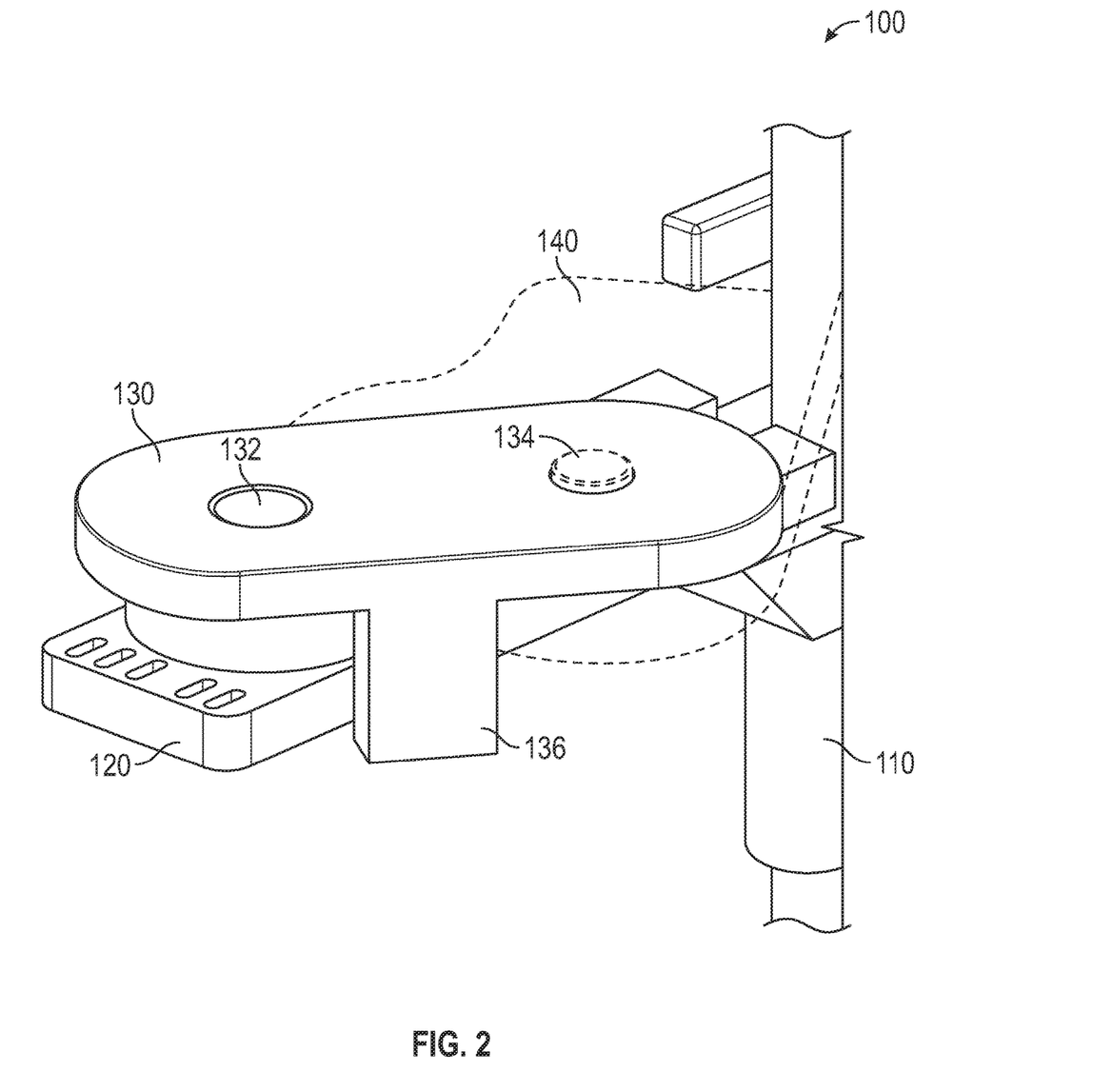
FIG. 2 is a reverse perspective view of the flow stop assembly of FIG. 1 in the flow position, in accordance with various aspects of the present disclosure.

FIG. 2 is a reverse perspective view of the flow stop assembly 100 of FIG. 1 in the flow position, in accordance with various aspects of the present disclosure. During operation, the rotation of the rocker 130 and therefore the pincher 140 can be limited to prevent damage to the tubing 102 or to the flow stop assembly 100. In the depicted example, the rocker 130 can include a clamping limit wall 136 that extends from the rocker 130 to engage the base extension 120 at a rotational limit. For example, the clamping limit wall 136 can be configured to engage with the base extension 120 at a rotational position of the rocker 130 determined to effectively occlude or clamp the tubing 102 without damaging the tubing 102. Further, the clamping limit wall 136 may provide tactile and/or auditory feedback to the clinician.

Figure 3:
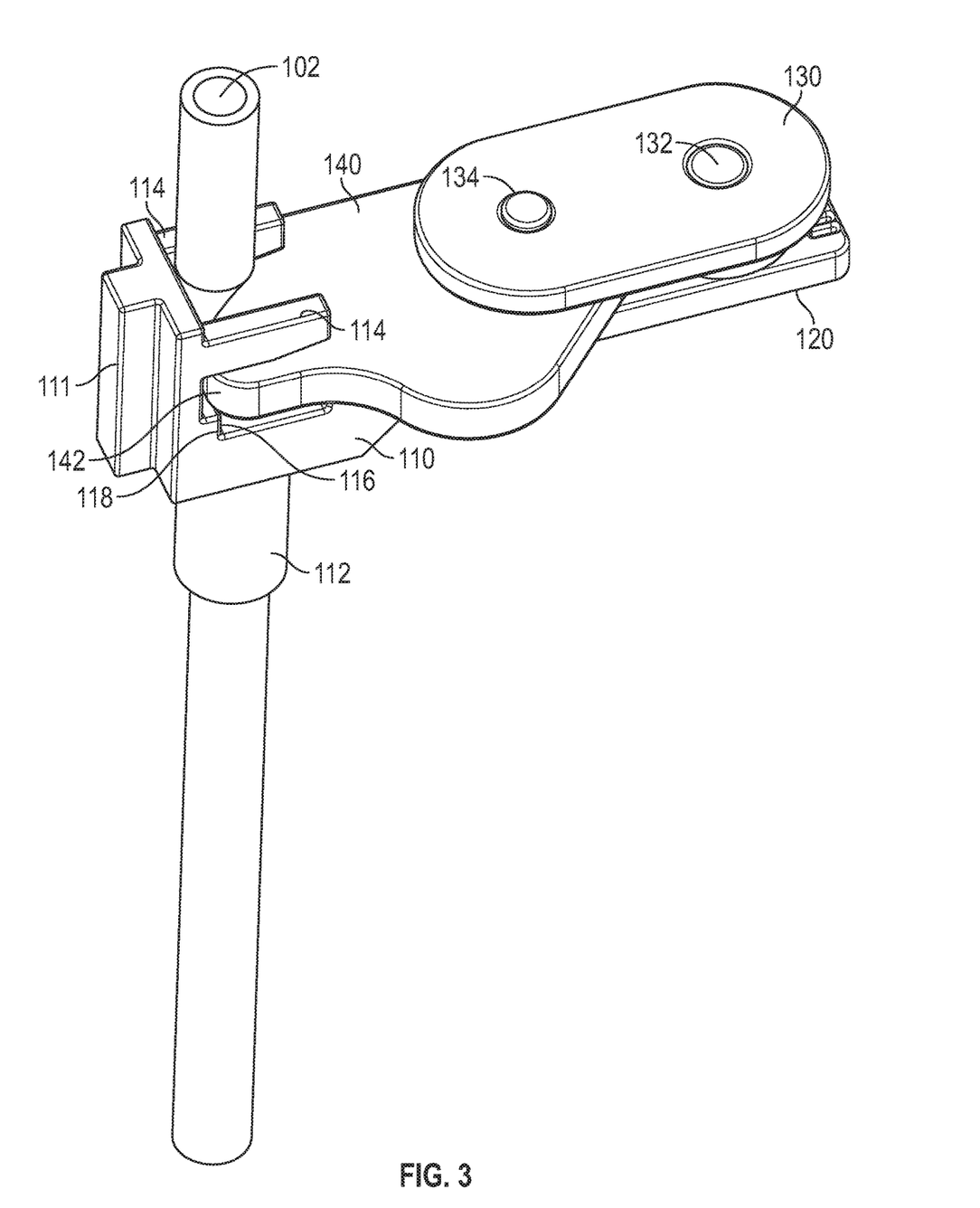
FIG. 3 is a perspective view of a flow stop assembly in an occlusion position, in accordance with various aspects of the present disclosure.
Figure 4:
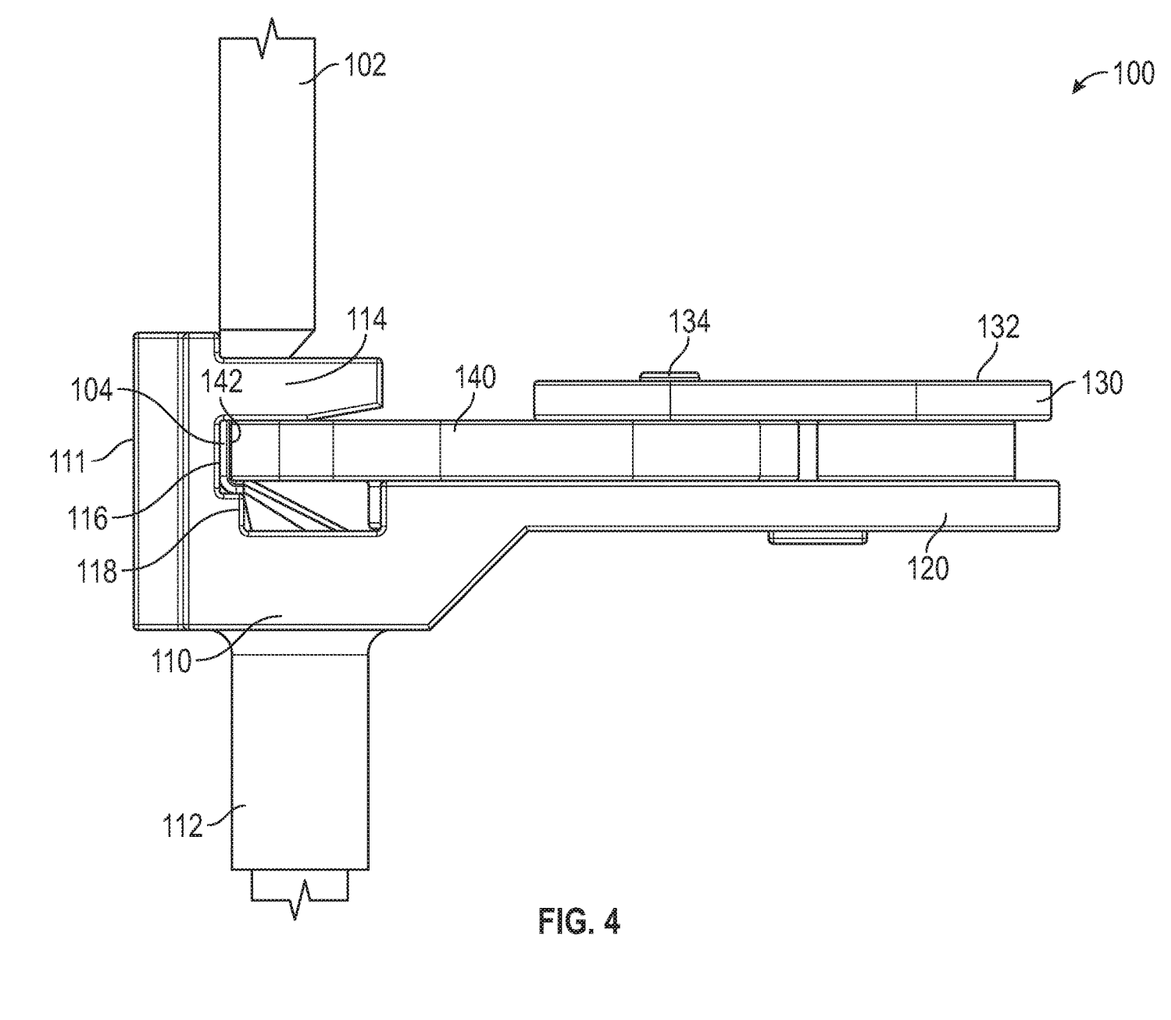
FIG. 4 is an elevation view of the flow stop assembly of FIG. 3 in the occlusion position, in accordance with various aspects of the present disclosure.

FIG. 3 is a perspective view of a flow stop assembly 100 in an occlusion position, in accordance with various aspects of the present disclosure. FIG. 4 is an elevation view of the flow stop assembly 100 of FIG. 3 in the occlusion position, in accordance with various aspects of the present disclosure. With reference to FIGS. 3 and 4, in an occlusion position or configuration, the flow stop assembly 100 can occlude the flow of medical fluid through the tubing 102. Advantageously, the flow stop assembly 100 can be utilized to occlude the flow of medical fluid during an infusion procedure or any other suitable procedure.

In the depicted example, the pincher 140 is actuated to engage the pincher surface 142 against the tubing 102 to fold the tubing 102 into a folded position 104 over the pincher protrusion 118 formed within the pincher recess 116. As illustrated, the pincher protrusion 118 extends from the base wall 111. By folding or kinking the tubing 102 over the pincher protrusion 118, the flow within the tubing 102 can be occluded or obstructed to limit or stop fluid flow through the tubing 102.

During operation, to move from a flow position to an occlusion position, the pincher 140 is rotated or otherwise actuated into place. As the pincher surface 142 engages the tubing 102, the pincher guards 114, base wall 111, and/or the tubing guide 112 that define the pincher recess 116 prevent undesired radial movement of the tubing 102 during engagement.

In some embodiments, the rocker 130 is rotated to rotate and/or translate the pincher 140 into the occlusion position. As illustrated, the rocker 130 is rotated to be in line with the base extension 120 to rotate the pincher 140 toward the pincher recess 116 and fold the tubing 102 over the pincher protrusion 118. Advantageously, by utilizing the rocker 130 or linkage, a clinician can easily fold the tubing 102 over the pincher protrusion 118 with minimal force.

Figure 5:
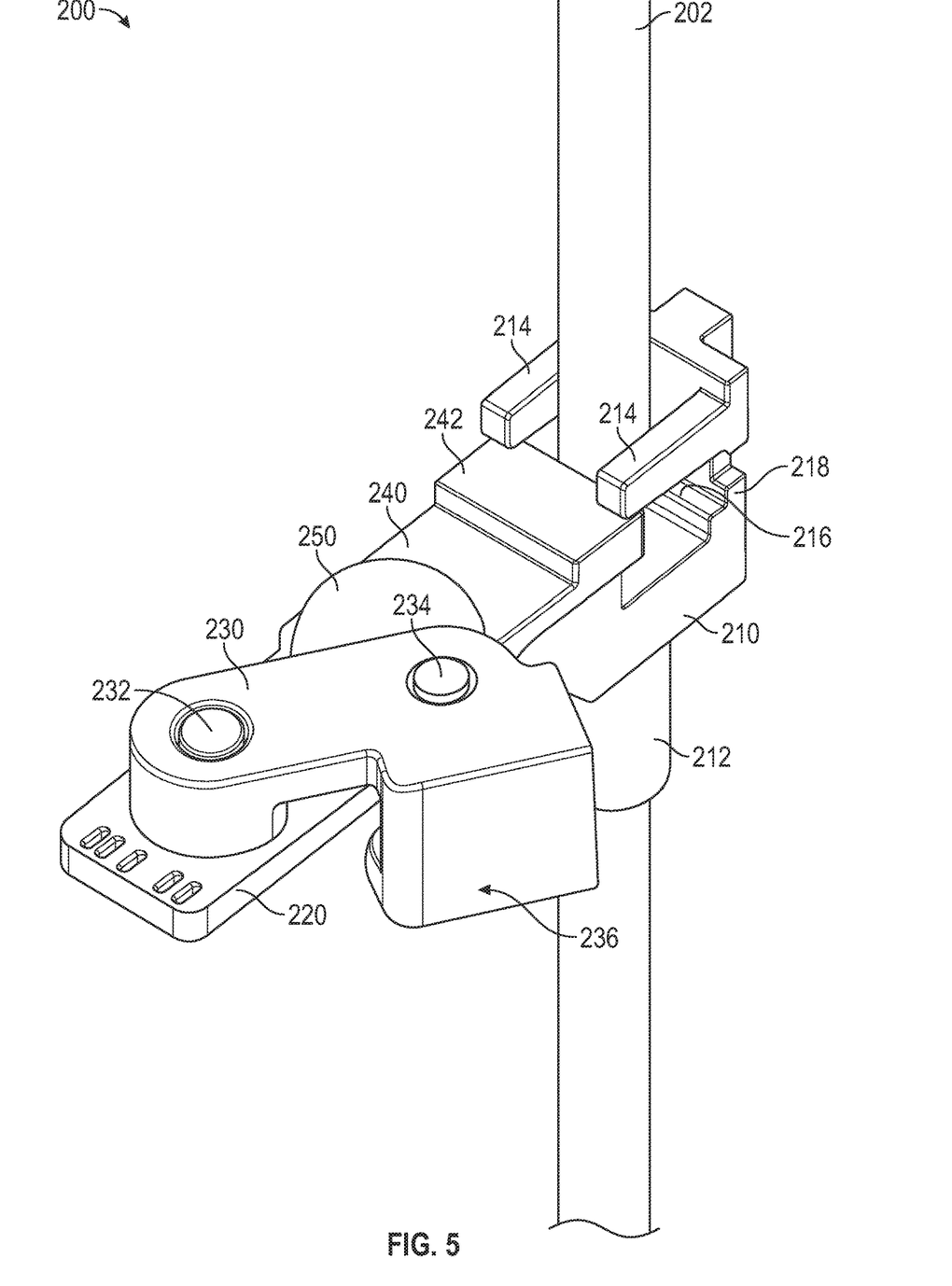
FIG. 5 is a perspective view of a flow stop assembly in a flow position, in accordance with various aspects of the present disclosure.

FIG. 5 is a perspective view of a flow stop assembly 200 in a flow position, in accordance with various aspects of the present disclosure. In the depicted example, the flow stop assembly 200 can utilize a translating or sliding pincher 240 to fold or occlude the tubing 202.

During operation, the pincher 240 can slide from a flow position to an occlusion position. In the occlusion position, the pincher surface 242 of the pincher 240 can engage with the tubing 202 to fold the tubing 202 over the pincher protrusion 218 as described herein.

In some embodiments, the pincher 240 can utilize a linkage to translate the pincher 240 from the flow position to the occlusion position. For example, the flow stop assembly 200 can utilize a four bar linkage to actuate the pincher 240. In the depicted example, the pincher 240 can be constrained to translational movement.

As illustrated, a crank 230 and a rocker 250 can cooperatively allow for the translation of the pincher 240. In some embodiments, the crank 230 is rotatably coupled to the base extension 220 of the flow stop base 210. As illustrated, the crank 230 can rotate about a crank pivot 232 rotatably coupling the crank 230 to the base extension 220. As the crank 230 is rotated, the crank 230 can actuate the rocker 250. In some embodiments, the crank 230 can be rotatably coupled to the rocker 250 at a rocker link 234. In the depicted example, the rotation of the crank 230 can actuate or otherwise rotate the rocker 250. During operation, the cooperative rotation of the crank 230 and the rocker 250 provides a translation force to the pincher 240 to translate the pincher 240 as desired.

During operation, the rotation of the crank 230 and therefore the translation of the pincher 240 can be limited to prevent damage to the tubing 202 or to the flow stop assembly 200. In the depicted example, the crank 230 can include a clamping limit wall 236 that extends from the crank 230 to engage the base extension 220 at a rotational limit. For example, the clamping limit wall 236 can be configured to engage with the base extension 220 at a rotational position of the crank 230 determined to effectively occlude or clamp the tubing 202 without damaging the tubing 202. Further, the clamping limit wall 236 may provide tactile and/or auditory feedback to the clinician.

Figure 6:
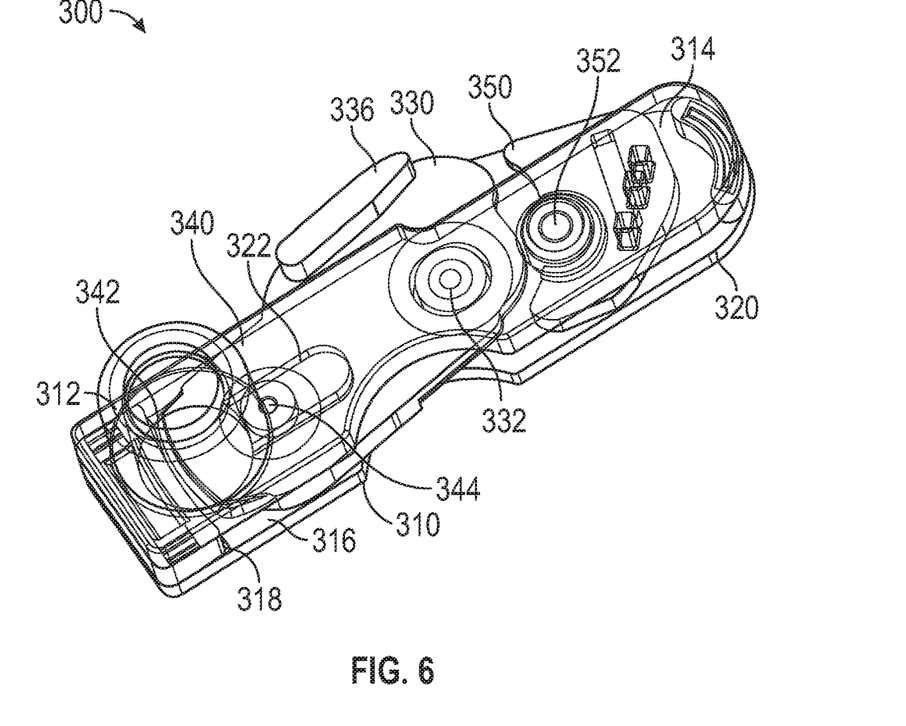
FIG. 6 is a perspective view of a flow stop assembly, in accordance with various aspects of the present disclosure.

FIG. 6 is a perspective view of a flow stop assembly 300, in accordance with various aspects of the present disclosure. In the depicted example, the flow stop assembly 300 can utilize a rotating cam or pincher 340 to fold or occlude the tubing.

During operation, the pincher 340 can rotate and/or slide from a flow position to an occlusion position. In the occlusion position, the pincher surface 342 of the pincher 340 can engage with the tubing (not pictured) to fold the tubing over the pincher protrusion 318 as described herein.

In some embodiments, the pincher 340 can utilize a cam mechanism to rotate the pincher 340 from the flow position to the occlusion position. In the depicted example, the pincher 340 can rotate and/or translate.

As illustrated, a crank portion 330 of the pincher 340 and a rocker 350 can cooperatively allow for the translation of the pincher 340. In some embodiments, the crank portion 330 rotatably couples the pincher 340 to the base extension 320 of the flow stop base 310. As illustrated, the crank portion 330 can rotate about a crank pivot 332 rotatably coupling the pincher 340 to the base extension 320. As the crank portion 330 is rotated, the pincher 340 can actuate the rocker 350. In some embodiments, the pincher 340 can have a cam surface disposed opposite to the pincher surface 342 that engages with a cam surface of the rocker 350 such that the rotation of the pincher 340 can actuate or otherwise rotate the rocker 350. During operation, the cooperative rotation of the pincher 340 and the rocker 350 provides a translation force to the pincher 340 to translate the pincher 340 as desired.

During operation, the rotation of the crank portion 330 and therefore the translation of the pincher 340 can be limited to prevent damage to the tubing or to the flow stop assembly 300. In the depicted example, the pincher 340 can include a clamping limit wall 336 that extends from the crank portion 330 to engage the cap 314 at a rotational limit. For example, the clamping limit wall 336 can be configured to engage with the cap 314 at a rotational position of the pincher 340 determined to effectively occlude or clamp the tubing without damaging the tubing. Further, the clamping limit wall 336 and the cap 314 may provide tactile and/or auditory feedback to the clinician.

Optionally, the cap 314 can be disposed over the pincher 340 and/or the rocker 350 to at least partially cover the components of the flow stop assembly 300. In some embodiments, a pincher guard or upper tubing guide 312 formed through the cap 314 can retain and/or align tubing that passes through the flow stop assembly 300, functioning as a pincher guard as described with respect to other embodiments described herein. As illustrated, the upper tubing guide 312 can be a tubular protrusion or cylindrical member that extends axially from the cap 314 to form a partial sleeve around the tubing. The upper tubing guide 312 can prevent lateral or radial movement of tubing during operation, including during pinching or occlusion operations. The upper tubing guide 312 can be sized to prevent radial movement of the tubing while allowing axial movement of the tubing.

Figure 7:
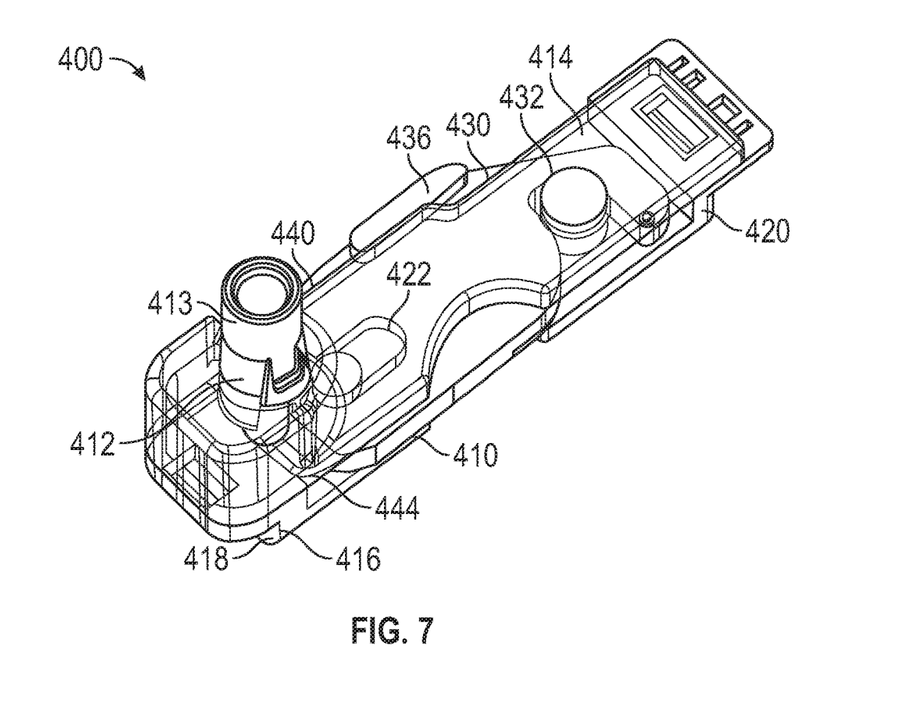
FIG. 7 is a perspective view of a flow stop assembly, in accordance with various aspects of the present disclosure.

FIG. 7 is a perspective view of a flow stop assembly 400, in accordance with various aspects of the present disclosure. In the depicted example, the flow stop assembly 400 can utilize a rotating pincher 440 to fold or occlude the tubing.

During operation, the pincher 440 can rotate from a flow position to an occlusion position. In the occlusion position, the pincher surface 442 of the pincher 440 can engage with the tubing (not pictured) to fold the tubing over the pincher protrusion 418 as described herein.

In some embodiments, the pincher 440 is rotatably coupled to the base extension 420 of the flow stop base 410. As illustrated, the pincher 440 can rotate about a pivot 432 allowing the pincher surface 442 to travel along an arc. During operation, the rotation of the pincher 440 about the pivot 432 can provide a mechanical advantage to the clinician.

During operation, the rotation of the pincher 440 can be limited to prevent damage to the tubing or to the flow stop assembly 400. In the depicted example, the pincher 440 can include a clamping limit wall 436 that extends from the pincher 440 to engage the cap 414 at a rotational limit. For example, the clamping limit wall 436 can be configured to engage with the cap 414 at a rotational position of the pincher 440 determined to effectively occlude or clamp the tubing without damaging the tubing. Further, the clamping limit wall 436 and the cap 414 may provide tactile and/or auditory feedback to the clinician.

Optionally, the cap 414 can be disposed over the pincher 440 to at least partially cover and/or retain the components of the flow stop assembly 400. In some embodiments, a pincher guard or upper tubing guide 412 formed through the cap 414 can retain and/or align tubing that passes through the flow stop assembly 400, functioning as a pincher guard as described with respect to other embodiments described herein. As illustrated, the upper tubing guide 412 can be a tubular protrusion or cylindrical member that extends axially from the cap 414 to form a partial sleeve around the tubing. The upper tubing guide 412 can prevent lateral or radial movement of tubing during operation, including during pinching or occlusion operations. The upper tubing guide 412 can be sized to prevent radial movement of the tubing while allowing axial movement of the tubing.

Optionally, the flow stop assembly 400 can include a tubing coupler 413 that is retained and aligned within pincher recess 416. During operation, portions of tubing can be fluidly coupled to the tubing coupler 413 allowing fluid communication therethrough. As can be appreciated, flow through the tubing coupler 413 can be stopped by the pinching or occlusion operation as described herein. Advantageously, by coupling tubing to the tubing coupler, aligning and/or positioning tubing within the flow stop assembly 400 can be simplified.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A flow stop assembly configured to control flow through a tubing, the flow stop assembly comprising:
    a flow stop base comprising:
        a base wall extending from the flow stop base;
        at least one pincher guard, wherein the at least one pincher guard is configured to be disposed around the tubing;
        a tubing guide configured to receive the tubing, wherein the at least one pincher guard and the tubing guide are axially spaced apart and are configured to axially align the tubing through the flow stop base;
        a pincher recess defined between the base wall, the at least one pincher guard, and the tubing guide;
        a pincher protrusion disposed within the pincher recess and configured to be adjacent to the tubing, wherein the pincher protrusion extends from the base wall; and
        a base extension extending away from the pincher recess and defining a guide slot;
    a pincher movable relative to the base extension and comprising a pincher surface and a guide pin extending through the guide slot, the pincher configured to move between a flow position and an occlusion position, wherein in the flow position the pincher surface is spaced apart from the pincher protrusion and in the occlusion position, the pincher surface is disposed adjacent to the pincher protrusion and is configured to obstruct flow through the tubing; and
    a rocker rotatably coupled to the base extension and the pincher, wherein rotation of the rocker moves the pincher and the pincher is rotatable about the rocker in a first rotational axis and the guide pin in a second rotational axis different from the first rotational axis.

2. The flow stop assembly of claim 1, wherein the rocker comprises a clamping limit wall extending from the rocker, the clamping limit wall configured to limit the rotation of the rocker.

3. The flow stop assembly of claim 1, wherein rotation of the rocker rotates the pincher.

4. The flow stop assembly of claim 1, further comprising: a crank rotatably coupled to the base extension and the rocker, wherein rotation of the crank moves the pincher.

5. The flow stop assembly of claim 4, wherein the crank comprises a clamping limit wall extending from the crank, the clamping limit wall configured to limit the rotation of the crank and the movement of the pincher.

6. The flow stop assembly of claim 1, wherein the pincher is translatable about the guide slot.

7. A flow stop assembly, comprising:
    a tubing defining a flow path;
    a flow stop base comprising:
        a base wall extending from the flow stop base;
        at least one pincher guard, wherein the at least one pincher guard is disposed around the tubing;
        a tubing guide configured to receive the tubing, wherein the at least one pincher guard and the tubing guide are axially spaced apart and are configured to axially align the tubing through the flow stop base;
        a pincher recess defined between the base wall, the at least one pincher guard, and the tubing guide, wherein the tubing extends through the pincher recess;
        a pincher protrusion disposed within the pincher recess adjacent to the tubing, wherein the pincher protrusion extends from the base wall; and
        a base extension extending away from the pincher recess and defining a guide slot; and
    a pincher rotatable relative to the base extension and comprising a pincher surface and a guide pin extending through the guide slot, the pincher configured to move between a flow position and an occlusion position, wherein in the flow position the pincher surface is spaced apart from the tubing and in the occlusion position, the pincher surface engages the tubing to fold the tubing over the pincher protrusion to obstruct the flow path of the tubing; and
    a rocker rotatably coupled to the base extension and the pincher, wherein rotation of the rocker moves the pincher and the pincher is rotatable about the rocker in a first rotational axis and the guide pin in a second rotational axis different from the first rotational axis.

8. The flow stop assembly of claim 7, wherein the rocker comprises a clamping limit wall extending from the rocker, the clamping limit wall configured to limit the rotation of the rocker.

9. The flow stop assembly of claim 7, wherein rotation of the rocker rotates the pincher.

10. The flow stop assembly of claim 7, further comprising: a crank rotatably coupled to the base extension and the rocker, wherein rotation of the crank translates the pincher.

11. The flow stop assembly of claim 10, wherein the crank comprises a clamping limit wall extending from the crank, the clamping limit wall configured to limit the rotation of the crank and the translation of the pincher.

12. The flow stop assembly of claim 7, wherein the pincher is translatable about the guide slot.

13. A method, comprising:
    providing fluid flow through a tubing, wherein the tubing extends through a flow stop base defining a guide slot;
    rotating a rocker rotatably coupled to the flow stop base to actuate a pincher against the tubing to fold the tubing over a pincher protrusion, wherein the pincher is rotatable about the rocker in a first rotational axis and the guide slot in a second rotational axis different from the first rotational axis; and
    obstructing the fluid flow through the tubing.

14. The method of claim 13, further comprising rotating the pincher to engage against the tubing.

15. The method of claim 13, further comprising sliding the pincher to engage against the tubing.

16. The method of claim 13, further comprising limiting an actuation range of the pincher.

17. The method of claim 13, further comprising translating the pincher about the guide slot.

* * * * *